United States Patent
Tian et al.

(10) Patent No.: US 8,404,895 B2
(45) Date of Patent: Mar. 26, 2013

(54) TERTIARY AMINE SALT ADDITIVES FOR HYDRATE CONTROL

(75) Inventors: Jun Tian, League City, TX (US); Cheryl R. Bailey, Sugar Land, TX (US)

(73) Assignee: Baker Hughes Incorporated, Houston, TX (US)

( * ) Notice: Subject to any disclaimer, the term of this patent is extended or adjusted under 35 U.S.C. 154(b) by 250 days.

(21) Appl. No.: 13/012,472

(22) Filed: Jan. 24, 2011

(65) Prior Publication Data

US 2012/0190893 A1 Jul. 26, 2012

(51) Int. Cl.
*C07C 211/63* (2006.01)
*C07C 9/00* (2006.01)

(52) U.S. Cl. ........... 564/292; 564/295; 585/15; 585/950

(58) Field of Classification Search ........... 564/292, 564/295

See application file for complete search history.

(56) References Cited

U.S. PATENT DOCUMENTS

| | | | |
|---|---|---|---|
| 5,550,289 A * | 8/1996 | Eppstein et al. | 564/293 |
| 6,444,852 B1 | 9/2002 | Milburn et al. | |
| 7,662,970 B2 | 2/2010 | Rivers et al. | |
| 2004/0159041 A1 | 8/2004 | Dahlmann et al. | |
| 2005/0085676 A1 | 4/2005 | Panchalingam et al. | |
| 2005/0101495 A1 | 5/2005 | Dahlmann et al. | |
| 2010/0191014 A1 * | 7/2010 | Iwase et al. | 564/286 |

* cited by examiner

*Primary Examiner* — Brian J Davis

(74) *Attorney, Agent, or Firm* — Mossman Kumar & Tyler PC

(57) ABSTRACT

New tertiary amine salts are useful as gas hydrate inhibitors in oil and gas production and transportation. These tertiary amine salts give very good separation from an emulsion, are economic and have reduced toxicity concerns.

7 Claims, 4 Drawing Sheets

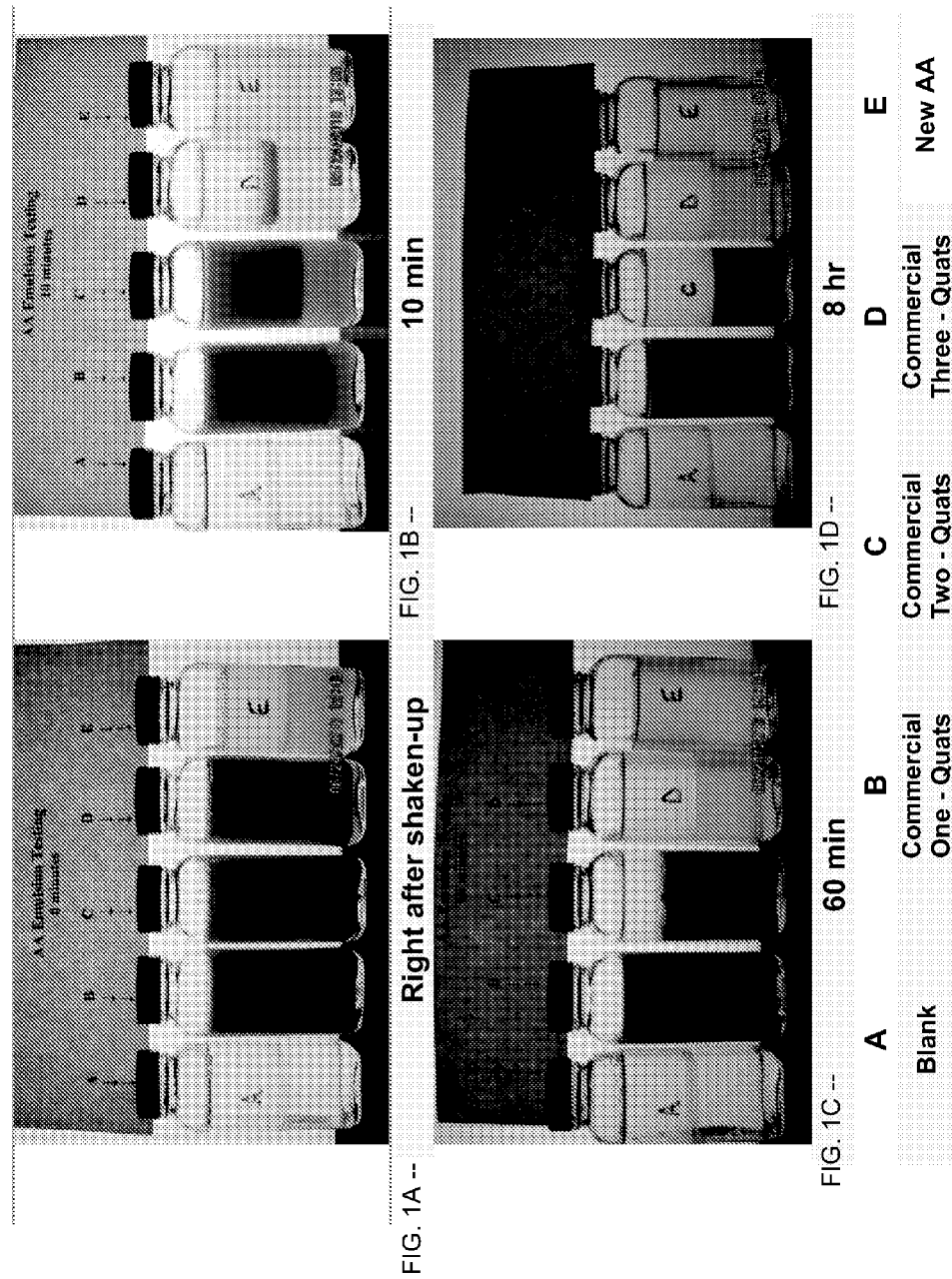

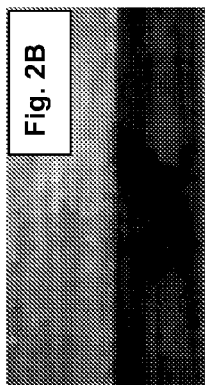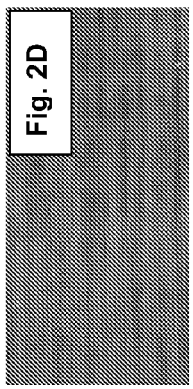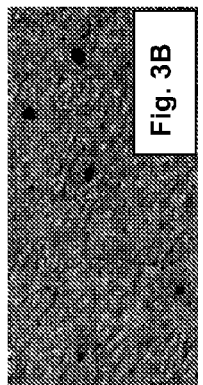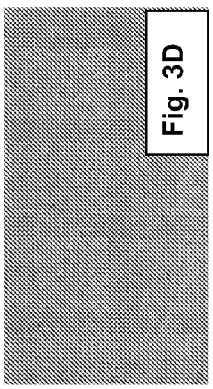
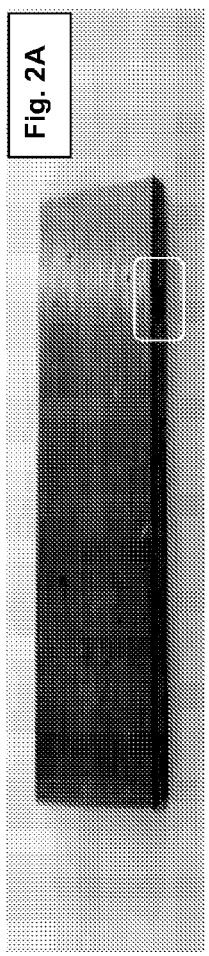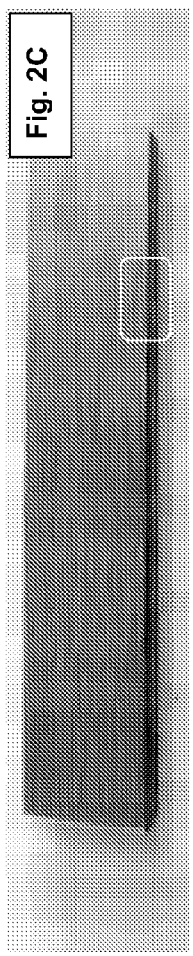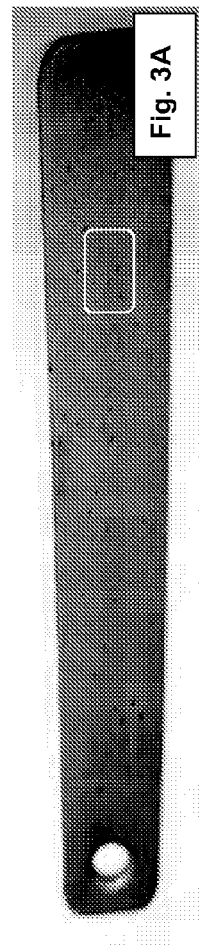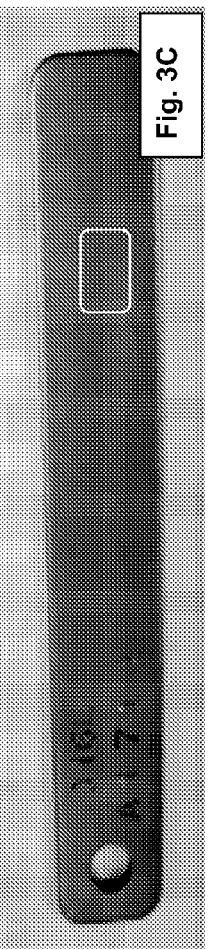

TERTIARY AMINE SALT ADDITIVES FOR HYDRATE CONTROL

TECHNICAL FIELD

The invention relates to tertiary amine salts, and most particularly relates, in one non-limiting embodiment, to organic and inorganic tertiary amine salts useful for inhibiting the formation of hydrocarbon hydrates during the production of oil and gas.

BACKGROUND

A number of hydrocarbons, especially lower-boiling light hydrocarbons, in formation fluids or natural gas are known to form hydrates in conjunction with the water present in the system under a variety of conditions—particularly at the combination of lower temperature and higher pressure. The hydrates usually exist in solid forms that are essentially insoluble in the fluid itself. As a result, any solids in a formation or natural gas fluid are at least a nuisance for production, handling and transport of these fluids. It is further not uncommon for hydrate solids (or crystals) to cause plugging and/or blockage of pipelines or transfer lines or other conduits, valves and/or safety devices and/or other equipment, resulting in shutdown, loss of production and risk of explosion or unintended release of hydrocarbons into the environment either on-land or off-shore. Accordingly, hydrocarbon hydrates have been of substantial interest as well as concern to many industries, particularly the petroleum and natural gas industries.

Hydrocarbon hydrates are clathrates, and are also referred to as inclusion compounds. Clathrates are cage structures formed between a host molecule and a guest molecule. A hydrocarbon hydrate generally is composed of crystals formed by water host molecules surrounding the hydrocarbon guest molecules. The smaller or lower-boiling hydrocarbon molecules, particularly $C_1$ (methane) to $C_4$ hydrocarbons and their mixtures, are more problematic because it is believed that their hydrate or clathrate crystals are easier to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under certain conditions.

There are two broad techniques to overcome or control the hydrocarbon hydrate problems, namely thermodynamic and kinetic. For the thermodynamic approach, there are a number of reported or attempted methods, including water removal, increasing temperature, decreasing pressure, addition of "antifreeze" to the fluid and/or a combination of these. The kinetic approach generally attempts (a) to prevent the smaller hydrocarbon hydrate crystals from agglomerating into larger ones (known in the industry as an anti-agglomerate and abbreviated AA) and/or (b) to inhibit and/or retard initial hydrocarbon hydrate crystal nucleation; and/or crystal growth (known in the industry as a kinetic hydrate inhibitor and abbreviated KHI). Thermodynamic and kinetic hydrate control methods may be used in conjunction.

Kinetic efforts to control hydrates have included use of different materials as inhibitors. For instance, onium compounds with at least four carbon substituents are used to inhibit the plugging of conduits by gas hydrates. Additives such as polymers with lactam rings have also been employed to control clathrate hydrates in fluid systems. These kinetic inhibitors are commonly labeled Low Dosage Hydrate Inhibitors (LDHI) in the art. KHIs and even LDHIs are relatively expensive materials, and it is always advantageous to determine ways of lowering the usage levels of these hydrate inhibitors while maintaining effective hydrate inhibition.

Quaternary amine chemistry has been proven to be effective as AA for hydrate control. However, water quality and fluids separation upon its application are industrial-wide technical challenges, therefore thwarting its broad field implementation to replace conventional THI methods. Derivatives from quaternary amine technology that itself possesses potentially severe corrosive tendency, such as betaine, also present similar challenges, irrespective of higher raw material cost (RMC) and complex synthesis routes.

Thus, it is desirable if new gas hydrate inhibitors were discovered which would yield comparable or improved results over known gas hydrate inhibitors, and it is also desirable to find new ways of forming gas hydrate inhibitors.

SUMMARY

There is provided, in one form, a method for inhibiting formation of hydrocarbon hydrates that involves contacting a fluid that includes a mixture having water and hydrate-forming guest molecules at gas hydrate forming conditions with an amount of a tertiary amine salt effective to inhibit formation of hydrocarbon hydrates at the conditions. The tertiary amine salt may be an organic tertiary amine salts of formula (I):

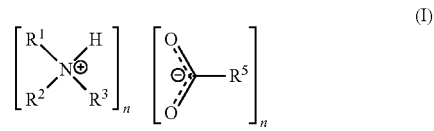

where $R^1$ and $R^2$ are independently $C_1$-$C_6$ straight, branched or cyclic alkyl;
$R^3$ is selected from the group consisting of

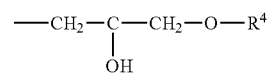

and a bridged group with another N+ of:

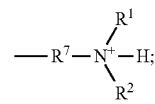

$R^4$ is a $C_6$-$C_{18}$ straight, branched or cyclic alkyl or straight, branched or cyclic alkyl bridged to another $N^+$;
$R^5$ is H, $R^1$ or

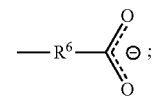

$R^6$ is straight $C_1$-$C_4$ alkylene;
$R^7$ is a $C_1$-$C_{18}$ straight, branched or cyclic alkylene; and
n is 1 to 10 and is the same as the number of $N^+$.

The tertiary amine salts also include inorganic tertiary amine salts, that is, where the anion is inorganic, having formula (II):

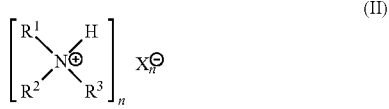

where X is selected from the group consisting of $H_2PO_4^-$, $HPO_4^=$, $PO_4^\equiv$, $ClO_4^-$, $NO_3^-$, and combinations thereof, and n is as above. Combinations of organic tertiary amine salts and inorganic tertiary amine salts as defined above may also be usefully employed.

In a different non-restrictive embodiment, there are presented new compositions of matter that involve the organic tertiary amine salts and the inorganic tertiary amine salts describe above.

BRIEF DESCRIPTION OF THE DRAWINGS

FIGS. 1A through 1D are photographs of five bottles, one containing a blank bilayer of oil and water, three containing the same oil and water bilayer with 1.0 vol % of conventional hydrate inhibitors, and the last, fifth bottle containing the same oil and water bilayer with 1.0 vol % of one of the new tertiary amine salt hydrate inhibitors described herein, at various time intervals after agitation, showing the quick separation of the layers containing the tertiary amine salt hydrate inhibitor compared to the separation of the bottles with the conventional hydrate inhibitors, which were visibly relatively slower;

FIG. 2A is a photograph of a SS304L stainless steel coupon that had been held for one week at 250° F. (121° C.), 400 psig $N_2$ (2.8 MPa) with no air purge in a commercial AA-1 hydrate inhibitor;

FIG. 2B is an enlarged photograph of the rectangular section of FIG. 2A;

FIG. 2C is a photograph of a SS304L stainless steel coupon that had been held for one week at 250° F. (121° C.), 400 psig $N_2$ (2.8 MPa) with no air purge in a pure new hydrate inhibitor AA;

FIG. 2D is an enlarged photograph of the rectangular section of FIG. 2C;

FIG. 3A is a photograph of a SS316L stainless steel coupon that had been held for one week at 200° F. (93° C.), 400 psig $N_2$ (2.8 MPa) with no air purge in a commercial AA-1 hydrate inhibitor;

FIG. 3B is an enlarged photograph of the rectangular section of FIG. 3A;

FIG. 3C is a photograph of a SS316L stainless steel coupon that had been held for one week at 200° F. (93° C.), 400 psig $N_2$ (2.8 MPa) with no air purge in a new hydrate inhibitor AA;

FIG. 3D is an enlarged photograph of the rectangular section of FIG. 3C; and

DETAILED DESCRIPTION

Figure 4:
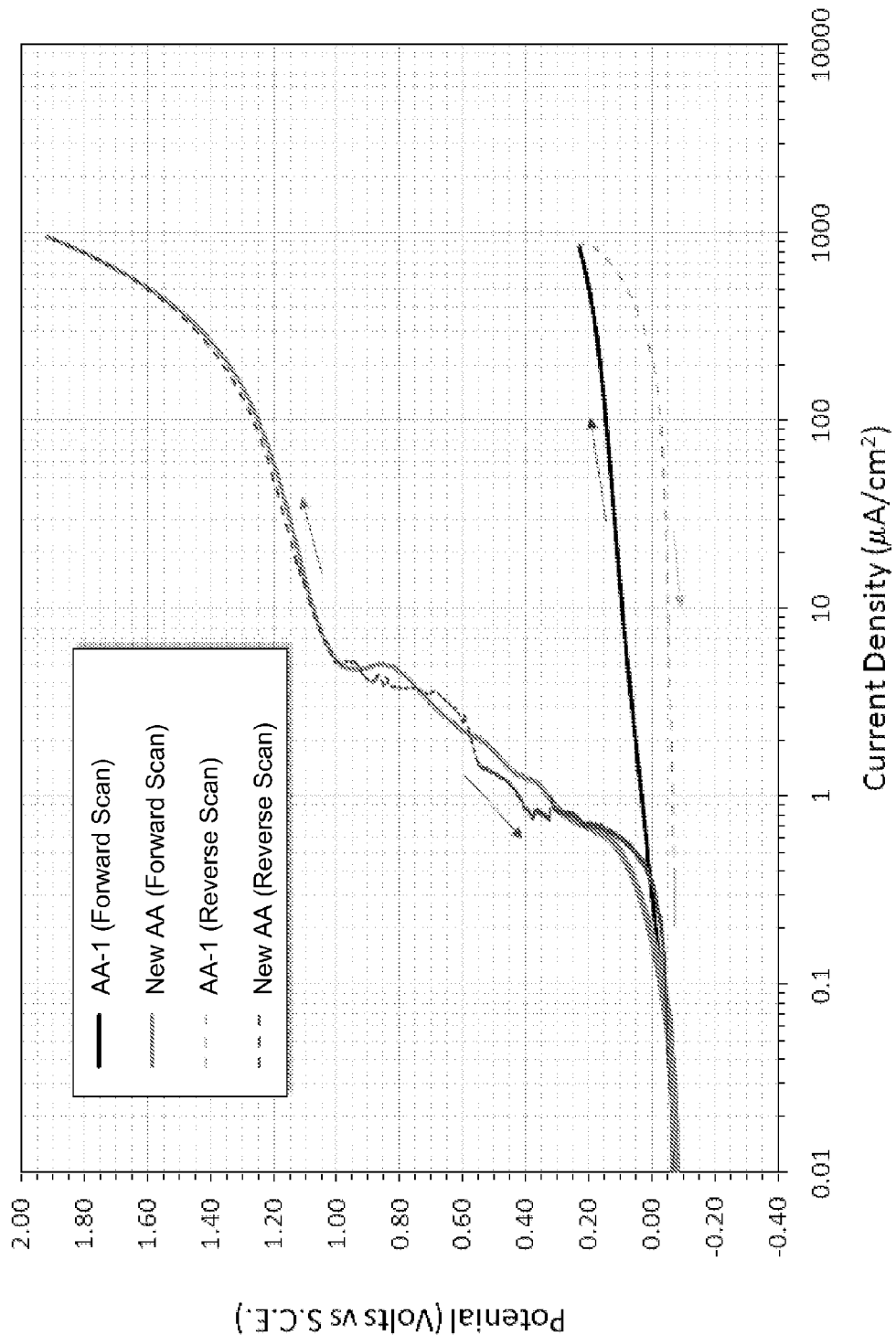
FIG. 4 is a standard potentiodynamic polarization plot according to ASTM G61-86 (2009) graphing both forward and reverse scans for both commercial hydrate inhibitor AA-1 and new hydrate inhibitor AA.

Described herein are methods and compositions used for inhibiting, retarding, mitigating, reducing, controlling and/or delaying formation of hydrocarbon hydrates or agglomerates of hydrates in fluids used in hydrocarbon recovery operations.

The methods and compositions may be applied to prevent or reduce or mitigate plugging of annular spaces, pipes, transfer lines, valves, and other places or equipment downhole where hydrocarbon hydrate solids may form under conditions conducive to their formation or agglomeration.

The term "inhibiting" is used herein in a broad and general sense to mean any improvement in preventing, controlling, delaying, abating, reducing or mitigating the formation, growth and/or agglomeration of hydrocarbon hydrates, particularly light hydrocarbon gas hydrates in any manner, including, but not limited to kinetically, thermodynamically, by dissolution, by breaking up, by anti-agglomeration, other mechanisms, or any combination thereof. Although the term "inhibiting" is not intended to be restricted to the complete cessation of gas hydrate formation, it may include the possibility that formation of any gas hydrate is entirely prevented.

The terms "formation" or "forming" relating to hydrates are used herein in a broad and general manner to include, but are not limited to, any formation of hydrate solids from water and hydrocarbon(s) or hydrocarbon and non-hydrocarbon gas(es), growth of hydrate solids, agglomeration of hydrates, accumulation of hydrates on surfaces, any deterioration of hydrate solids plugging or other problems in a system and combinations thereof.

The present method is useful for inhibiting hydrate formation for many hydrocarbons particularly including hydrocarbon and non-hydrocarbon mixtures. The method is particularly useful for lighter or low-boiling, $C_1$-$C_5$, hydrocarbon gases, non-hydrocarbon gases or gas mixtures at ambient conditions. Examples of such gases include, but are not necessarily limited to, methane, ethane, ethylene, acetylene, propane, propylene, methylacetylene, n-butane, isobutane, 1-butene, trans-2-butene, cis-2-butene, isobutene, butene mixtures, isopentane, pentenes, natural gas, carbon dioxide, hydrogen sulfide, nitrogen, oxygen, argon, krypton, xenon, and mixtures thereof. These molecules are also termed hydrate-forming guest molecules herein. Other examples include various natural gas mixtures that are present in many gas and/or oil formations and natural gas liquids (NGL). The hydrates of all of these low-boiling hydrocarbons are also referred to as gas hydrates. The hydrocarbons may also comprise other compounds including, but not limited to CO, $CO_2$, COS, hydrogen, hydrogen sulfide ($H_2S$), and other compounds commonly found in gas/oil formations or processing plants, either naturally occurring or used in recovering/processing hydrocarbons from the formation or both, and mixtures thereof.

More specifically, the tertiary amine salts herein would be useful hydrate inhibitors in many fluids involved in hydrocarbon recovery operations including, but not limited to, drilling fluids, drill-in fluids, workover fluids, completion fluids, produced fluids and the like. Suitable salts in or for forming the brines of these fluids include, but are not necessarily limited to, sodium chloride, calcium chloride, zinc chloride, potassium chloride, potassium bromide, sodium bromide, calcium bromide, zinc bromide, sodium formate, potassium formate, ammonium formate, cesium formate, and mixtures thereof.

The tertiary amine salts are completely new versions of AA inhibitors to overcome the limitations of current commercial AA inhibitors, such as corrosion tendencies, difficulty separating in oil/water mixtures, and toxicity concerns. Using self molecular assembling concept, several new classes of ammonium salts have been synthesized and evaluated on hydrate control performance against the bench-mark AA commercial product AA-1 inhibitor. It has been found that under the typical AA evaluation conditions, the new tertiary amine salt hydrate inhibitors have demonstrated at least the same performance as AA-1 inhibitor. Based on the chemistry, the new tertiary amine salt hydrate inhibitors have reduced raw materials cost and apparently reduced toxicity concerns than AA-1.

Moreover, preliminary lab studies also reveal, using AA-1, AA-2 and AA-3 as controls, that the new tertiary amine salts have provided much improved water and fluids separation performance. Derived from this initial understand and observation, more new chemistries are being investigated.

Suitable gas hydrate inhibitors for use in the methods and fluid compositions herein may include, but are not necessarily limited to, two embodiments of tertiary amine salts, one having organic anions and the other having inorganic anions. The embodiments having the structure of formula (I) have the organic anions:

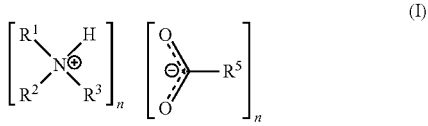
(I)

where $R^1$ and $R^2$ are independently $C_1$-$C_6$ straight, branched or cyclic alkyl;
$R^3$ is selected from the group consisting of

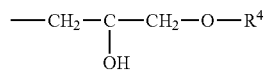

and a bridged group with another $N^+$ of:

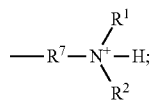

$R^4$ is a $C_6$-$C_{18}$ straight, branched or cyclic alkyl or straight, branched or cyclic alkyl bridged to another $N^+$;
$R^5$ is H, $R^1$ or

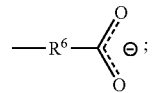

$R^6$ is straight $C_1$-$C_4$ alkylene;
$R^7$ is a $C_1$-$C_{18}$ straight, branched or cyclic alkylene; and
n is 1 to 10 and is the same as the number of $N^+$, and
The inorganic tertiary amine salts comprise formula (II):

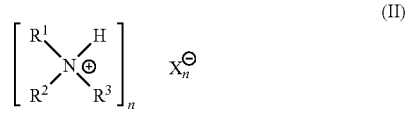
(II)

where X is selected from the group consisting of $H_2PO_4^-$, $HPO_4^=$, $PO_4^\equiv$, $ClO_4^-$, $NO_3^-$, and combinations thereof, and n is as above; and combinations thereof.

The novel tertiary amine salts may be readily made by reacting secondary amines, such as those with the formulae $HNR^1R^2$ where $R^1$ and $R^2$ are as above with a number of co-reactants, including, but not necessarily limited to, (a) reaction with an epoxide, (b) reaction with an epoxide where the reaction product is subsequently combined with a monocarboxylic acid or a dicarboxylic acid to give a tertiary amine salt of formula (I), and (c) reaction with an unsaturated nitrile (for instance acrylonitrile: $CH_2$=CH—C$\equiv$N), where the reaction product is subsequently combined with a monocarboxylic acid or a dicarboxylic acid to give a tertiary amine salt of formula (I). Further, (d) reaction of two moles of a secondary amine with one mole of formaldehyde produces a methylene bridged bi-tertiary amine of formula (III):

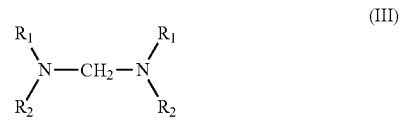
(III)

One mole of these methylene bridged bi-tertiary amines may be further combined with one or two moles of a carboxylic acid. If reaction is subsequently with two moles of a carboxylic acid, the reaction may be with one more of acetic acid and one mole of a carboxylic acid with more carbon atoms.

It is believed that the amine salts form due at least to hydrogen bonding of the hydrogens of hydroxyl groups of the amines with oxygens of the carboxylic anion, and/or the hydrogen of the tertiary $N^+$ atom. It has been discovered that the amine salts made with the methylene bridged bi-tertiary amines are particularly suitable as hydrate inhibitors.

In alternate embodiments, instead of combining the tertiary amines with mono- or dicarboxylic acids to form the tertiary amine salts, the tertiary amines are combined with phosphoric acid ($H_3PO_4$) in mole ratios of 1:1, 1:2 and 1:3 (molar ratio to N in the amine), perchloric acid ($HClO_4$) and/or nitric acid ($HNO_3$).

Suitable starting secondary amines include, but are not necessarily limited to, n-butylamine, di-n-butylamine, tri-n-butylamine, N—(N,N-di-n-butylamino)-methylene-di-n-butylamine, n-butylaminoethanol and di-n-butylaminoethanol and combinations thereof. Suitable mono-and dicarboxylic reactants and anion providers include, but are not necessarily limited to, acetic acid, formic acid, benzoic acid, lactic acid, citric acid (variously with 1:1, 1:2 and 1:3 molar ratios to N), stearic acid, glycolic acid, oxalic acid, succinic acid, adipic acid, phthalic acid, terephthalic acid, diglycolic acid, coconut acid, L-tartaric acid, malonic acid and combinations thereof. Suitable epoxides include, but are not necessarily limited to, aliphatic monoglycidyl ether containing straight, branched or cyclic alkyl chains with carbon number from 4 to 18 and combinations thereof.

Generally, the tertiary amine salts are prepared under reaction conditions sufficient to produce the tertiary amines and then the appropriate salts, depending on what the anion of the salt will be. Suitable reaction conditions include a temperature ranging from about ambient to about 150° C., inclusive, and a pressure ranging from about ambient to the pressure required to keep the reactants and solvents in the liquid phase, inclusive. In an alternative, non-restrictive embodiment, the reaction temperature may range between ambient and about 90° C. The tertiary amine salts may be formed directly under vigorous stirring at ambient conditions.

The contacting of the tertiary amine salt gas hydrate inhibitors herein with the mixture of hydrocarbon, water and hydrate-forming guest molecules may be achieved by a number of ways or techniques, including, but not necessarily limited to, mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition in the mixture. The contacting can be made in-line or offline or both. The various components of the composition may be mixed prior to or during contact, or both. The tertiary amine salt gas hydrate inhibitor should be prepared or formed prior to addition to the mixture or liquid that has potential for hydrate formation. If needed or desired, the tertiary amine salt may be optionally removed or separated mechanically, chemically, or by other methods known to one skilled in the art, or by a combination of these methods after the hydrate formation conditions and/or hydrate-forming species are no longer present.

Because the present compositions and methods are particularly suitable for inhibiting hydrate formation by lower boiling hydrocarbons or hydrocarbon and/or non-hydrocarbon gases at ambient conditions with no more than five carbon atoms, the pressure of the hydrate-forming condition is usually at or greater than atmospheric pressure (i.e. greater than or equal to about 101 kPa), in one non-limiting embodiment greater than about 1 MPa, and in an alternate version greater than about 5 MPa. The pressure in certain formations or processing plants or units could be much higher, say greater than about 20 MPa. There is no specific high pressure limit. The present method can be used at any pressure that allows formation of hydrocarbon gas hydrates.

The temperature of the condition for contacting is usually below, the same as, or not much higher than the ambient or room temperature. Lower temperatures tend to favor hydrate formation, thus requiring the treatment with the present compositions. At much higher temperatures, however, hydrocarbon hydrates may not form, thus obviating the need of carrying out any treatments.

It will be appreciated that it may be difficult to predict in advance the proportions of tertiary amine salt gas hydrate inhibitors herein effective in inhibiting hydrocarbon hydrate formations in a particular fluid any given situation. There are a number of complex, interrelated factors that must be taken into account in determining the effective dosage or proportion, including, but not necessarily limited to, the proportion of water in the fluid, the nature of the hydrocarbon, the nature of the hydrate-forming guest molecules, the temperature and pressure conditions that the mixture of hydrocarbon and water are subject to, the particular hydrocarbon hydrate inhibitor employed, etc. Experimentation with a particular set of conditions or in a specific system may be a suitable way to determine the optimum dosage range. Care should be taken to avoid the formation of problematic quantities of irreversible, harmful hydrate masses. Nevertheless, in the interest of attempting to provide some general guidance of effective proportions, relative to the water phase, the amount of the hydrate inhibitor is about 10 volume % or less, alternatively 8 volume % or less, and in another non-limiting embodiment is less than 6 vol %. In one non-limiting embodiment the lower limit is independently about 0.01 volume %, and alternatively is about 0.1 vol % and possibly is about 0.5 vol %. Any combination of these lower and upper limits may form a suitable range.

Lab testing has demonstrated or is expected to demonstrate that the tertiary amine salt hydrate inhibitors overcome the drawbacks of current, commercial AA inhibitors, particularly quaternary ammonium chemistry, including, but not necessarily limited to, (1) corrosion concerns due to a large $Cl^-$ presence (the present tertiary amine salts have little or no chlorine anion presence), (2) increased toxicity concerns of the water phase since quaternary ammonium compounds are soluble in the water, whereas the present tertiary amine salts tend to dissolve in the hydrocarbon phase, and (3) thermal instability due to Hoffmann Elimination. With respect to the latter concern of thermal instability, the quaternary ammonium compounds tend to come apart at higher temperatures and thus the resulting products do not function as hydrate inhibitors; they thus have limited applicability for downhole injection.

In addition to the gas hydrate inhibitor herein, the hydrocarbon inhibitor composition and the fluid being treated may further comprise other additional components, including, but not limited to, different controlling chemistries such as corrosion inhibitors, wax inhibitors, scale inhibitors, asphaltene inhibitors and other gas hydrate inhibitors and/or solvents. It has been discovered that certain of the tertiary amine salt inhibitors may also function as one or more of the following: corrosion inhibitor, scale inhibitor, asphaltene inhibitor, and paraffin inhibitor.

Suitable solvents for the gas hydrate inhibitors herein may include, but are not limited to at least one oxygenated compound selected from $C_1$-$C_6$ alcohols, $C_2$-$C_6$ glycols, $C_1$-$C_6$ mono-aliphatic, in one non-limiting embodiment monoalkyl, ethers of $C_2$-$C_6$ glycol, glycerin, $C_1$-$C_6$ mono-aliphatic, suitably mono-alkyl, ethers of glycerin, $C_1$-$C_6$ di-aliphatic, particularly dialkyl, ethers of glycerin, glycerin esters of $C_1$-$C_6$ carboxylate; N-methylpyrrolidone; sulfolane; $C_3$-$C_{10}$ ketones, and mixtures thereof. Examples of acceptable solvents in one non-limiting embodiment include liquid oxygenated materials such as methanol, ethanol, propanol, glycols like ethylene glycol, 1,2-propylene glycol, 1,3-propylene glycol, glycerin, esters and ethers of glycerin, CELLOSOLVE® (2-ethoxyethanol), CELLOSOLVE derivatives, 2-propoxyethanol, 2-isopropoxyethanol, 2-butoxyethanol, 2-isobutoxyethanol, 2-methoxyethanol, ethoxylated propylene glycols, ketones such as cyclohexanone and diisobutylketone, and mixtures thereof. Both alkyl and aromatic hydrocarbons may also be used as solvents, including, but not necessarily limited to, hexanes, heptanes, octanes, kerosene, toluene xylene and other aromatic mixtures. The mixture of oxygenated compounds and hydrocarbon liquids at different volumetric ration can also be used for the hydrate inhibitor carrier. The solvent is present in the total hydrocarbon hydrate inhibiting composition in the range of from about 0 wt % to about 85 wt %, alternatively from about 0 wt % to about 65 wt %, of the total composition, based on volume. CELLOSOLVE is a registered trademark of Union Carbide Corporation.

The present methods and compositions also may be used in combination with other methods or processes, which have been known to one skilled in the art as discussed in the background to help inhibit formation of hydrates. The compositions and methods will now be further illustrated with respect to specific Examples which are intended to further illuminate the invention but not limit it in any way.

EXAMPLE 1

Stability Study 50 mL of brine and 50 mL of hydrocarbon were placed in each of five bottles. 1.0 vol % of four different gas hydrate inhibitors, including three commercial ones, AA-1, AA-2 and AA-3, and a new AA as described herein, as follows:

| Bottle | Gas hydrate inhibitor |
|---|---|
| A | Blank |
| B | Commercial AA-1 |
| C | Commercial AA-2 |
| D | Commercial AA-3 |
| E | New AA |

The bottles were mechanically shaken vigorously together in an identical manner, and then photographs taken at four separate times: (A) immediately afterwards, (B) 10 minutes afterward, (C) 60 minutes afterward, and (D) eight hours afterward. The photographs are shown in FIGS. 1A, 1B, 1C, and 1D, respectively. It may be seen that the water and oil containing AA separated almost immediately, whereas the bottles containing the conventional hydrate inhibitors took longer to separate or resolve. It may thus be concluded that unlike some conventional quaternary ammonium hydrate inhibitors the tertiary amine salts described herein do not have an undesirable emulsifying effect. Moreover, the water is clear of hydrate inhibitor, which has been all partitioned to the hydrocarbon phase, whereas the other three commercial AAs had a fair amount of residual material in the aqueous phase. This residual material made the water color changed slightly from colorless to light yellow.

The new AA of the Examples herein has the structure of formula (I) where $R^1$ and $R^2$ are n-butyl groups, $R^3$ is 2-hydroxy-3-alkoxypropyleneyl, $R^4$ is dodecanyl, tridecanyl and tetradecanyl mixture, $R^5$ contains bicarboxyl groups, $R^6$ is a bridge with carbon no less than 3 and n is 3.

Hydrate Inhibition Examples

AA Test Apparatus and General Procedures

MULTIFLASH software package from Infochem Computer Services Ltd. was used for performing the equilibrium calculations of thermodynamic models on gas hydrate stability curves for a given hydrocarbon composition under specific testing conditions. The results predicted the conditions (pressure and temperature) at which gas hydrates are formed and stable. Thus, for a particular field scenario, the degree of subcooling experienced was determined. MULTIFLASH has also been used to design laboratory tests to ensure that in-house gas mix produces similar hydrate stability curves and provide the required subcooling. (Subcooling is the difference between the temperature at which hydrates are stable minus the operating temperature. Subcooling gives an approximate estimate of the driving force for hydrate formation.)

The gas hydrate test apparatus was a bank of pressurized sight glass (sapphire) cells containing two stainless steel balls and an independent pressure transducer. In a typical experiment, each cell was charged with brine, oil (or condensate), and an inhibitor chemistry package. The cells were then pressurized to the target value with a gas blend and placed in a communal, temperature controlled water bath.

The communal water bath, and therefore the cells, were either rocked (to simulate flow conditions) or held static (to simulate a shut-in) during the course of each experiment. The rocking motion, when employed, caused the steels balls within cells to traverse each cell's longitudinal axis, creating additional agitation. During shut-ins, the cells are placed at a horizontal stagnant position.

Data logging included monitoring the water bath temperature, the pressure of each cell and periodic visual observations. As all experiments were isochoric; the cell pressure decreased as the cell temperature is lowered.

Visual observations included documenting a rating assessment of the cell's contents (Table I): a determination if hydrates are visible, an evaluation of any visible hydrate's surface adhesion properties and an estimate of liquid levels. A pass is typically rated as an A, B or C for AA. Any evidence of hydrates irreversibly sticking to the sapphire tube or the balls, forming a plug, or freezing the ball in place is a fail, which is by and large rated as a D or F. When two rankings are listed, e.g., "D/B", the ranking changed during the course of the visual observation. The first ranking represents the initial observation, while the second represents the observation after manually agitating the cell. In addition, a letter ranking may employ a (−), for slightly worse, or a (+), for slightly better, than average behavior. The (+) and (−) symbols help to further delineate a ranking. The absence of a (−) or (+) means the matrix is considered "average" for that letter grade.

TABLE I

Hydrate Inhibitor Ranking System

| | Hydrate Inhibitor Ranking | | | | |
|---|---|---|---|---|---|
| Cell Observation | A | B | C | D | F |
| Visible Crystals | No | Few, <1 mm | Some, but free-flowing | Yes | Yes |
| Solid Deposits | No | No | No | Yes | |
| Oil Phase Viscosity | Low | Low | Slight Increase | Distinguished Increase | |
| Water Phase Viscosity | Low | Low | Slight Increase | Distinguished Increase | |
| Single Phase Forming | No | No | Maybe | | |
| Mobile Slush or Silt | No | No | Slight | Heavy | |
| System Plug | No | No | No | No | Yes |

Results are reported on a scale from A to F (no E rating), with A being the best and F being a failure. The symbols + or − may be appended to indicate tests that were better or worse, respectively, than the mid-point of the ranking, but did not belong in the next category. The rankings A+ and F− are not used. Rankings are determined as follows.

A No visible crystals. No solid deposits on sapphire tube or steel. Two distinct low viscosity liquid phases.

B No solid deposits on sapphire tube or steel. Two low viscosity liquid phases. Few crystals, not larger than 1 mm or hazy systems where hydrate crystals are forming, but are too small to distinguish with the unaided eye. No evidence of plugs in the system.

C No solid deposits on sapphire tube or steel. Often some increase in liquid viscosities, but still free flowing. Small crystals not agglomerating to form a plug, or a milky or emulsified single-phase system. Some slight slush or silt may form, but it must be very mobile. No evidence of plugs in the system.

D No solid deposits on sapphire tube or steel. A heavy slush or silt is present, or there is a distinct increase in liquid viscosities. A long pipeline system would flow with difficulty. No evidence of immobile plugs in the system.

F Large immobile agglomerations of crystals that interfere with the flow of liquids are present. Ball is usually immobile. Deposits stuck on sapphire tube or steel.

Benchmark AA Laboratory Test Program

The AA laboratory test regime is the product of years of experience applying AA chemistries in the oilfield. Testing normally is designed to simulate the most severe field conditions expected. This test regime is conservative and is meant to fail the tested chemistry if at all possible. Accordingly, the test employs mild agitation of the fluid matrix to minimize mechanical assistance to the formation of fine hydrate partials. In addition, the test cells are typically "shock"-cooled under shut-in conditions, where the warm cells are placed in a water bath that has already been cooled to the target temperature.

Sub-Sampling Black Oil & Condensate Samples

The hydrate laboratory used only handled dead oil samples, that is, oil at sufficiently low pressure that it contains no dissolved gas or a relatively thick oil or residue that has lost its volatile components. The sub-sampling of oil and condensate samples is conducted by the most efficient means available and in a manner to maintain sample integrity. This means most samples were well agitated before subdivision at room temperature.

For waxy, "high" wax appearance temperature samples, efforts are made to pre-condition the hydrocarbon sample, especially when loading the test cell. Preconditioning usually included heating the sample to about 160° F. (about 71° C.) for over an hour with occasional agitation before sub-sampling. Such oils and condensates were loaded hot into the test cell, which is at room temperature. The cell was then placed into the test bath, and the test started as soon as reasonable thereafter. Other methods for handling waxy samples were available upon special requests, providing safety limitations not exceeded.

LDHI Quality Control

Quality control for LDHIs is achieved by performing blanks and/or duplicate tests. In this study, a blank testing experiment was used for the quality control.

The representative testing results under the same testing conditions with the new chemistry versus the different quaternary AA chemistries are summarized as below. They have been compared under different parameters: dose rate, fluids adaptability (salinity, water cuts, and different hydrocarbons with various API).

The standard procedures by shock-in at 40° F. (4° C.) for shut-in overnight at subcooling of 34.2° F. (1.2° C.) were used, followed by immediate visual observation and then continuous rocking-up. Visual observations are done after rocking for 8, 16, 24 and 48 hours. The tests were then shut-in for at least another 24 hours for further assessment, if the cell survives the scrutiny.

TABLE II

Dose Rate Comparison

| | | | Product | | | |
|---|---|---|---|---|---|---|
| | AA-1 | AA-2 | AA-3 | New AA | AA-1 | New AA |
| Dose Rate (vol % on water) | 1.5 | 1.5 | 1.5 | 1.5 | 1.0 | 1.0 |
| Brine @ 25% WC | | | 3.0 wt % NaCl | | | |
| Final Ranking | C | F | F | A | F | B |

TABLE III

Low Salinity Effects

| | Water Composition at 25% WC | | | | | |
|---|---|---|---|---|---|---|
| | 1.0 wt % | | | Fresh Water | | |
| Product | New AA | AA-1 | | New AA | AA-1 | |
| Dose Rate (vol % on water) | 2.5 | 3.0 | 3.0 | 2.5 | 3.0 | 3.0 |
| Final Ranking | A | A | F | B | A | F |

TABLE IV

Water Cut Effects at 3.0 Wt % Salinity

| | Product | | | | | |
|---|---|---|---|---|---|---|
| | AA-1 | | | New AA | | |
| WC, % | 25 | 50 | 75 | 25 | 50 | 75 |
| Dose Rate (vol % on water) | 1.5 | 2.0 | 4.0 | 1.0 | 2.0 | 4.0 |
| Final Ranking | C | B | F | A | A | F |

TABLE V

Salinity Effects at High Water Cuts

| | Product New AA | | | | | |
|---|---|---|---|---|---|---|
| Salinity, wt % | 3.0 | 5.0 | 7.5 | 7.5 | 10.0 | 10.0 |
| WC, % | 75 | 75 | 75 | 90 | 90 | 90 |
| Dose Rate (vol % on water) | 4.0 | 4.0 | 4.0 | 4.0 | 4.0 | 4.0 |
| Final Ranking | F | F | B | C | C | F |

TABLE VI

Hydrocarbon Effects

| | Product New AA Hydrocarbon | | | | | |
|---|---|---|---|---|---|---|
| | Oil One | Oil Two | Oil Three | Oil Four | Oil Five | Oil Six |
| WC, % | 50 | 50 | 50 | 50 | 50 | 50 |
| Salinity, wt % | 5.0 | 5.0 | 5.0 | 5.0 | 5.0 | 5.0 |
| Dose Rate (vol % on water) | 2.0 | 2.0 | 2.0 | 2.0 | 2.0 | 2.0 |
| Final Ranking | A | A | A | A | A | A |

EXAMPLE 2

Corrosion

Shown in FIG. 2A is a photograph of a SS304L stainless steel coupon that had been held for one week at 250° F. (121° C.), 400 psig $N_2$ (2.8 MPa) with no air purge in a pure commercial AA-1 hydrate inhibitor, where FIG. 2B is an enlarged photograph of the small rectangular section of FIG. 2A. Similarly, FIG. 2C is a photograph of a very similar SS304L stainless steel coupon that had been held for one week at 250° F. (121° C.), 400 psig $N_2$ (2.8 MPa) with no air purge in the new hydrate inhibitor AA, where FIG. 2D is, in turn, an enlarged photograph of the small rectangular section of FIG. 2C. It may be readily seen that the coupon in the photographs of FIGS. 2A and 2B where the commercial hydrate inhibitor AA-1 was more corroded than the coupon of FIGS. 2C and 2D where the new hydrate inhibitor AA was used.

Shown in FIG. 3A is a photograph of a SS316L stainless steel coupon that had been held for one week at 200° F. (93° C.), 400 psig $N_2$ (2.8 MPa) with no air purge in commercial AA-1 hydrate inhibitor, where FIG. 3B is an enlarged photograph of the small rectangular section of FIG. 3A. Similarly, FIG. 3C is a photograph of a SS316L stainless steel coupon that had been held for one week at 200° F. (93° C.), 400 psig $N_2$ (2.8 MPa) with no air purge in the new hydrate inhibitor AA, where FIG. 3D is an enlarged photograph of the rectangular section of FIG. 3C. It may be readily seen that the coupon in the photographs of FIGS. 3A and 3B where the commercial hydrate inhibitor AA-1 was more corroded than the coupon of FIGS. 3C and 3D where the new hydrate inhibitor AA was used.

EXAMPLE 3

Corrosion

FIG. 4 is a standard potentiodynamic polarization plot of potential as a function of current density according to ASTM G61-86 (2009) graphing both forward and reverse scans for both commercial hydrate inhibitor AA-1 and new hydrate inhibitor AA for stainless steel SS304. Increasing the testing voltage from 1.2 to 2.0 volts does not provide the change of potentiodynamic polarization for the new AA, meaning that it is quite inert to electric current. However, the AA-1 shows potentiodynamic polarization changes even treated at much lower voltage, and cannot recapitate, meaning it has a higher potential to be pitted than new AA under the same conditions.

EXAMPLE 4

Fluids Quality

Figures 5A, 5B:
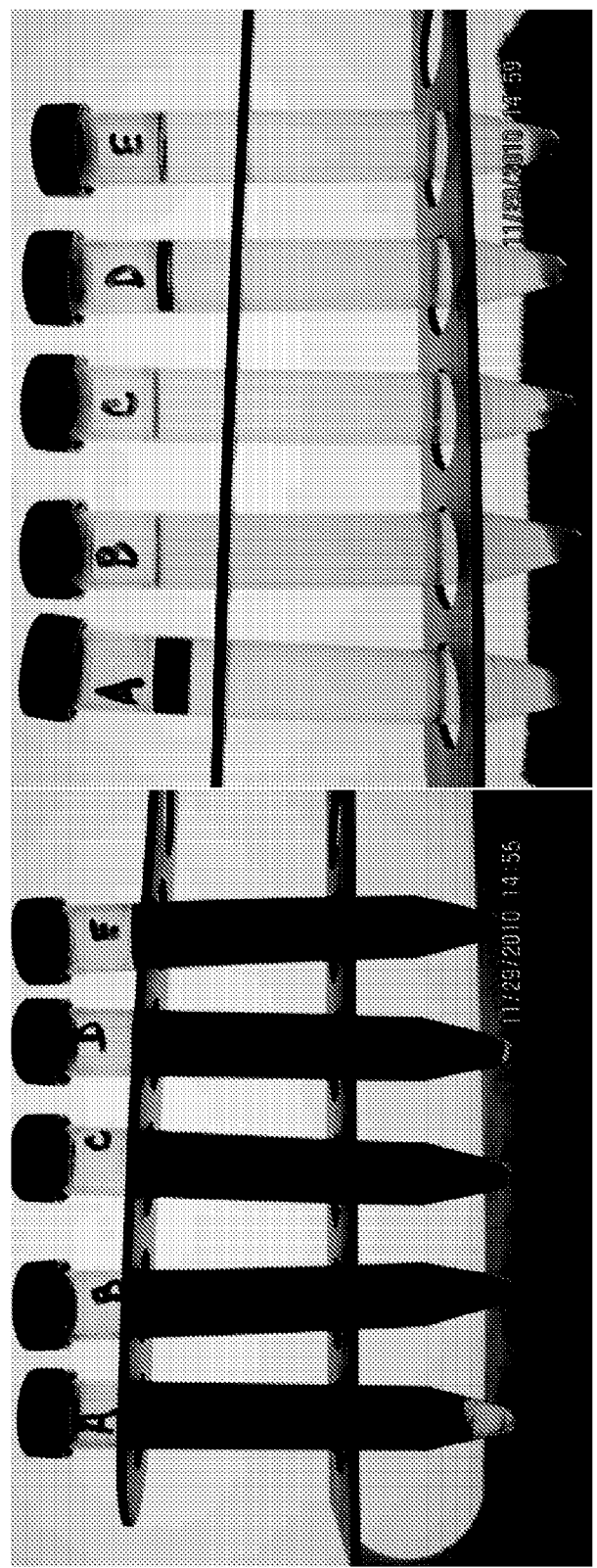
FIG. 5 is a photograph of fluids quality after the treatment of different AA chemicals (FIG. 5B) at the dose rate of 1.0 vol % of water compared with blank sample (FIG. 5A).

FIG. 5 is photographs of fluids quality after the treatment of different AA chemicals at the dose rate of 1.0 vol % of water (FIG. 5B) compared with blank sample (FIG. 5A). The oil and brine (1.2 wt % in NaCl) were first mixed at room temperature in 1:1 volume ratio with different AAs. After the phase separation, the oil and water phases were then centrifuged for fluids contamination. As quantified in Table VI, the fluids after treated with AAs, all have much lower water content in oil. AA-1 reduced the water content from 8.0 vol % to 0.3 vol %. And the New AA has reduced the water content, even lower to 0.1 vol %. As for the water quality, the same trends have been observed for the AA-treated samples compared with the blank. Both AA-1 and New AA have reduced the oil content from 8.0 vol % in blank sample to as low as 0.1 vol %. However, for all the water samples from AA-1, 2 and 3, they are yellow other than uncolored and transparent, indicating quite an amount of AA residue in the water sample. However, the water sample from New AA-treated run is as transparent and uncolored as the blank, illustrating remarkable water quality improvement over the current commercial ones.

TABLE VII

| A | B | C | D | E |
|---|---|---|---|---|
| Blank | AA-1 | AA-2 | AA-3 | New AA |
| | | Water in Oil, vol % | | |
| 8.0 | 0.3 | 0.5 | 0.8 | 0.1 |
| | | Oil in Water, vol % | | |
| 8.0 | 0.1 | 0.4 | 2.0 | 0.1 |

Many modifications may be made in the compositions and methods of this invention without departing from the spirit and scope thereof that are defined only in the appended claims. For example, the exact tertiary amine salts may be different from those explicitly mentioned herein. Various combinations of gas hydrate inhibitors alone or together other than those described here are also expected to be useful. Further, tertiary amine salts used alone or together with mixtures of water, hydrocarbons and hydrate-forming guest molecules different from those exemplified herein would be expected to be successful within the context herein. Additionally, preparatory methods different than those exemplified herein with respect to reactants and reaction conditions but nevertheless falling within the boundaries of the inventive method are still included. For instance, different secondary amines, nitriles, inorganic acids, monocarboxylic acids, dicarboxylic acids and epoxides from those explicitly mentioned herein may be used, and further, reaction conditions different from those exemplified and specifically mentioned are also expected to be useful.

The words "comprising" and "comprises" as used throughout the claims is interpreted "including but not limited to".

The present invention may suitably comprise, consist or consist essentially of the elements disclosed and may be practiced in the absence of an element not disclosed. For instance, the method may consist of or consist essentially of contacting a fluid as defined in the claims with the tertiary amine salts as defined in the claims. In another non-limiting embodiment, the only gas hydrate inhibitor introduced or added are the tertiary amine salts described herein.

What is claimed is:

1. A method for inhibiting formation of hydrocarbon hydrates comprising contacting a fluid including a mixture comprising water and hydrate-forming guest molecules at gas hydrate forming conditions with an amount of a tertiary amine salt effective to inhibit formation of hydrocarbon hydrates at the conditions, where the tertiary amine salt is selected from the group consisting of organic tertiary amine salts comprising formula (I):

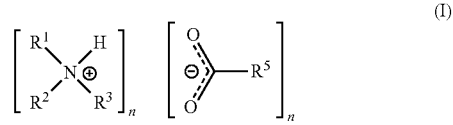

where $R^1$ and $R^2$ are independently $C_1$-$C_6$ straight, branched or cyclic alkyl;
$R^3$ is selected from the group consisting of:

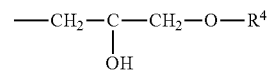

and a bridged group with another $N^+$ of:

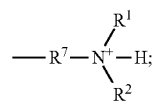

$R^4$ is a $C_6$-$C_{18}$ straight, branched or cyclic alkyl or straight, branched or cyclic alkyl bridged to another $N^+$;

$R^5$ is H, $R^1$ or

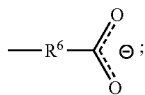

$R^6$ is straight $C_1$-$C_4$ alkylene;
$R^7$ is a $C_1$-$C_{18}$ straight, branched or cyclic alkylene; and
n is 1 to 10 and is the same as the number of $N^+$, and inorganic tertiary amine salts comprising formula (II):

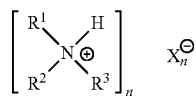 (II)

where X is selected from the group consisting of $H_2PO_4^-$, $HPO_4^=$, $PO_4^{\equiv}$, $ClO_4^-$, $NO_3^-$, and combinations thereof, and n is as above; and combinations thereof.

2. The method of claim 1 where the effective amount of the tertiary amine salt in the fluid ranges from about 0.01 to about 10 volume % based on the water present.

3. The method of claim 1 where the effective amount of the tertiary amine salt in the fluid ranges from about 0.1 to about 8 volume % based on the water present.

4. The method of claim 1 where the method further comprises an additional effect selected from the group consisting of:
   inhibiting corrosion,
   inhibiting scale formation,
   inhibiting asphaltene formation,
   inhibiting paraffin formation, and
   combinations thereof,
where the hydrate formation and the additional effect are greater as compared to an otherwise identical method absent the amine salt.

5. The method of claim 1 where in the organic tertiary amine salts of formula (I) and the inorganic tertiary amine salts of formula (II) $R^3$ is a bridged group with another $N^+$ or $R^4$ is a bridged group to another $N^+$.

6. A tertiary amine salt selected from the group consisting of organic tertiary amine salts comprising formula (I):

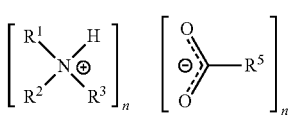 (I)

where $R^1$ and $R^2$ are independently $C_1$-$C_6$ straight, branched or cyclic alkyl;

$R^3$ is selected from the group consisting of:

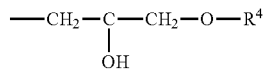

and a bridged group with another $N^+$ of:

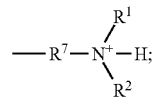

$R^4$ is a $C_6$-$C_{18}$ straight, branched or cyclic alkyl or straight, branched or cyclic alkenyl bridged to another $N^+$;

$R^5$ is H, $R^1$ or

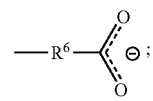

$R^6$ is straight $C_1$-$C_4$ alkylene;
$R^7$ is a $C_1$-$C_{18}$ straight, branched or cyclic alkylene; and
n is 1 to 10 and is the same as the number of $N^+$, and inorganic tertiary amine salts comprising formula (II):

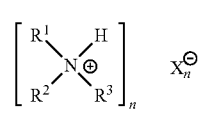 (II)

where X is selected from the group consisting of $H_2PO_4^-$, $HPO_4^=$, $PO_4^{\equiv}$, $ClO_4^-$, $NO_3^-$, and combinations thereof, and n is as above; and combinations thereof.

7. The tertiary amine salts of claim 6 where in the organic tertiary amine salts of formula (I) and the inorganic tertiary amine salts of formula (II) $R^3$ is a bridged group with another $N^+$ or $R^4$ is a bridged group to another $N^+$.

* * * * *